United States Patent [19]

Youngdale

[11] 4,081,471
[45] Mar. 28, 1978

[54] 2A,2B-DIHOMO-15-ALKYL-PGE$_1$ ANALOGS

[75] Inventor: Gilbert A. Youngdale, Portage, Mich.

[73] Assignee: The Upjohn Company, Kalamazoo, Mich.

[21] Appl. No.: 663,564

[22] Filed: Mar. 3, 1976

Related U.S. Application Data

[62] Division of Ser. No. 511,220, Oct. 2, 1974, Pat. No. 3,974,195.

[51] Int. Cl.$^2$ .............................................. C11C 3/02
[52] U.S. Cl. .............................. 260/410.9 R; 260/404; 260/404.5; 260/268 R; 260/410; 260/293.6; 260/413; 260/326.2; 260/514 D; 424/305; 424/318; 424/312; 544/98; 560/121
[58] Field of Search .................... 260/410 P, 410.9 P, 260/413 P, 404, 404.5 P, 468 D; 424/312

[56] References Cited

U.S. PATENT DOCUMENTS 3,514,383   5/1970   Beal et al. ...................... 260/410.9 P

OTHER PUBLICATIONS

Weeks, J. et al, The Journal of Pharmacology and Exp. Therapeutics, vol. 186 (1973), pp. 67–74.

*Primary Examiner*—Winston A. Douglas
*Assistant Examiner*—John F. Niebling
*Attorney, Agent, or Firm*—Robert A. Armitage

[57] ABSTRACT 2b, 2a-Dihomo-15-methyl and 15-ethyl PGF- and PGE-type compounds are disclosed with processes for making them. These compounds are useful for a variety of pharmacological purposes, including anti-ulcer, inhibition of platelet aggregation, increase of nasal patency, labor inducement at term, and wound healing.

7 Claims, No Drawings

2A,2B-DIHOMO-15-ALKYL-PGE₁ ANALOGS

The present application is a division of Ser. No. 511,220, filed Oct. 2, 1974, issued on Aug. 10, 1976 as U.S. Pat. No. 3,974,195.

The present invention relates to prostaglandin analogs, the essential material constituting a disclosure of which is incorporated here by reference from U.S. Pat. No. 3,974,195.

I claim:

1. An optically active compound of the formula:

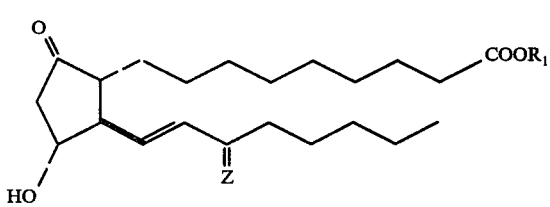

wherein Z is

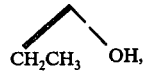

or

and wherein $R_1$ is hydrogen, alkyl of one to 12 carbon atoms, inclusive,

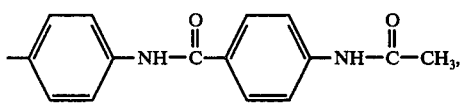

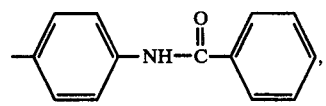

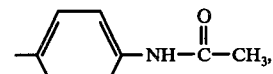

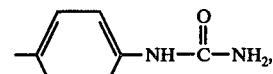

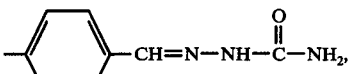

or

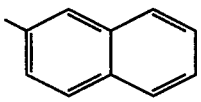

or pharmacologically acceptable salts thereof when $R_1$ is hydrogen.

2. A compound according to claim 1, wherein Z is

3. 2a,2b-Dihomo-15(S)-15-methyl-PGE₁, a compound according to claim 2, wherein $R_1$ is hydrogen.

4. 2a,2b-Dihomo-15(S)-15-methyl-PGE₁, methyl ester, a compound according to claim 2, wherein $R_1$ is methyl.

5. A compound according to claim 1, wherein Z is

6. 2a,2b-Dihomo-15(R)-15-methyl-PGE₁, a compound according to claim 5, wherein $R_1$ is hydrogen.

7. 2a,2b-Dihomo-15(R)-15-methyl-PGE₁, methyl ester, a compound according to claim 5, wherein $R_1$ is methyl.

* * * * *